United States Patent [19]

DeBoer

[11] 4,406,878

[45] Sep. 27, 1983

[54] IODINATED CONTRAST AGENT FOR RADIOGRAPHY

[75] Inventor: Charles D. DeBoer, Rochester, N.Y.

[73] Assignee: Eastman Kodak Company, Rochester, N.Y.

[21] Appl. No.: 76,718

[22] Filed: Sep. 19, 1979

Related U.S. Application Data

[63] Continuation of Ser. No. 930,290, Aug. 2, 1978, abandoned.

[51] Int. Cl.$^3$ ............................................. A61K 49/04
[52] U.S. Cl. ....................................................... 424/5
[58] Field of Search ............................................. 424/5

[56] References Cited

U.S. PATENT DOCUMENTS

| | | | |
|---|---|---|---|
| 3,212,973 | 10/1965 | Roberts et al. | 424/5 |
| 3,637,394 | 1/1972 | Smith et al. | 526/9 X |
| 3,733,397 | 5/1973 | Björk et al. | 424/5 |
| 4,022,814 | 5/1977 | Newton | 260/463 |

FOREIGN PATENT DOCUMENTS 1400985 7/1975 United Kingdom .

OTHER PUBLICATIONS

New York Academy of Sciences, *Annals*, 78, 1959, pp. 793-798.

*Primary Examiner*—Leonard Schenkman
*Attorney, Agent, or Firm*—Arthur H. Rosenstein

[57] ABSTRACT

An iodinated polymer which is water-insoluble and substantially non-water-swellable is disclosed as a useful contrast agent for a radiographic contrast composition and a surgical element. The polymer has an iodine content in excess of 35 percent by weight, preferably in excess of 50 percent by weight. Radiographic contrast compositions, elements, and imaging methods which employ this iodinated polymer as a contrast agent are disclosed.

7 Claims, No Drawings

IODINATED CONTRAST AGENT FOR RADIOGRAPHY

This is a continuation, of application Ser. No. 930,290, filed Aug. 2, 1978 now abandoned.

FIELD OF THE INVENTION

This invention relates to certain iodinated polymers of high iodine content as radiographic contrast agents and to radiographic contrast compositions, elements, and methods using these contrast agents.

BACKGROUND OF THE INVENTION

Medical radiography is a well-known and extremely valuable tool for the early detection and diagnosis of various disease states of the human body. However, body cavities and the soft tissues of body organs and blood vessels exhibit so little absorption of X-ray radiation that radiographs of these body portions are difficult to obtain. To overcome this problem, radiologists introduce an X-ray absorbing method, i.e, a "contrast agent," sometimes referred to as a radiopaque, into such body cavities and tissues. Such contrast agents have been used in the X-ray examination of the human body almost from the days of Roentgen.

A wide variety of inorganic materials, such as bismuth subnitrate, bismuth subcarbonate, barium sulfate, and the like, have been proposed for use as contrast agents. Of these, barium sulfate is probably the most widely used.

In addition, various iodinated organic materials have been proposed for use as contrast agents, the iodine molecule representing an effective X-ray absorber. Among these are iodinated oils, such as ethyl iodophenylundecylate, used for myelography, and water-soluble, iodinated organic compounds used for X-ray visualization of the gastrointestinal tract. Water-soluble, iodinated organic compounds, however, can cause extremely severe side effects when used as a gastrointestinal contrast agent in dehydrated patients, especially infants. For this reason, these materials have become quite controversial and some radiologists no longer use such agents in the gastrointestinal tract. See *Radiographic Contrast Agents*, Miller and Skucas, page 169 (1977), University Park Press, Baltimore, Md. 21202.

More recently, certain water-insoluble, iodinated organic polymers have been proposed for use as radiographic contrast agents. For example, British patent specification No. 1,400,985 published July 23, 1975 discloses certain polymers which contain iodine-substituted aromatic groups. The polymers disclosed in this patent, although water-insoluble, readily swell in water to give a gel. The iodine content of actual polymers disclosed in this patent is typically in the area of about 20 to 30 weight percent, with the highest being 35 weight percent.

Although water-swellable iodinated polymers of the type described in British patent specification No. 1,400,985 may have certain utility, iodinated polymers which are both water-insoluble and non-water-swellable would be advantageous. Also, iodinated polymers having a higher iodine concentration than those specifically disclosed in this British patent would be desirable. For example, iodinated polymers with these properties could readily be added to water to produce a low viscosity radiographic contrast composition suitable for injection into the blood stream or other small organs and body cavities, without fear that the mixture would swell and cause a blockage. In addition, higher iodine concentrations could reduce both the intensity of X-ray radiation and the amount of contrast agent required to obtain good radiographic visualization.

SUMMARY OF THE INVENTION

The present invention features certain iodinated polymers as a contrast agent. The invention provides a radiographic contrast composition and a surgical element comprising such a polymer as contrast agent and a carrier for this contrast agent. Radiographic imaging methods using these materials are also provided.

The iodinated polymer featured as the contrast agent in the present invention comprises a water-insoluble, substantially non-water-swellable, iodinated polymer having an iodine content in excess of 35 weight percent (based on the dry weight of the polymer). These polymers contain repeating units of the formula:

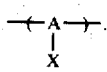

I wherein
- A represents a repeating organic unit in the backbone chain of the polymer, and
- X represents an organic moiety containing an iodinated aromatic group and a hydrophilic group, said moiety having an iodine content within the range of from about 40 to 80 weight percent (based on the molecular weight of X).

A preferred embodiment of the invention features a crosslinked, iodinated polymer of formula I wherein A represents the residue of a repeating unit in the backbone chain of a polymer having appended hydroxyl groups, the hydroxyl groups providing crosslinking sites and reaction sites for attachment of the moiety X.

The radiographic contrast composition of the invention can be either in dry or liquid state, depending upon the carrier for the iodinated polymer. For example, in the dry state the iodinated polymer can be compounded with a dry binder and prepared, for instance, in tablet form. In liquid state, which is the preferred state of the radiographic contrast composition for introduction into the body of a test subject, the iodinated polymer is dispersed in an aqueous liquid carrier as finely-divided, water-insoluble, non-water-swellable beads having a particle size of from about 0.01 to about 1000 microns.

In a further embodiment, a surgical element is provided which comprises a surgical article as a carrier, e.g., a surgical instrument, dressing, suture, or implant, and a radiographically effective amount of the above-described iodinated polymers as a control agent.

The present invention provides a useful method for forming radiographic images of a body portion, for example, a body cavity or body organ, of a test subject comprising the following steps:
(a) introducing into the body portion as a contrast agent a radiographically effective amount of a water-insoluble, non-water-swellable iodinated polymer having an iodine content in excess of 35 weight percent and a structural formula corresponding to formula I,
(b) exposing the body portion containing the contrast agent to X-ray radiation to form an image pattern corresponding to the presence of the iodinated polymer in the body, and (c) visualizing this image pattern.

DESCRIPTION OF THE PREFERRED EMBODIMENTS

Two important characteristics of the iodinated polymers employed in the invention are their high iodine content and their non-water-swellability, i.e., their resistance to water swellability. As indicated, these polymers typically have an iodine content in excess of about 35 weight percent, preferably in excess of 50 weight percent, based on the dry weight of the polymer. This increases the X-ray absorption properties of the polymer, thereby advantageously decreasing both the intensity of X-ray radiation and the amount of polymer contrast agent needed to provide effective visualization of a body organ or cavity.

The resistance to water-swellability exhibited by the iodinated polymers of the invention has reference to the fact that the polymer, in dry form, occupies a volume which is more than 90% of the volume occupied by the same amount of polymer which has been allowed to stand at room temperature (22° C.) for 24 hours in the presence of an amount of water equal to at least twice the weight of the dry polymer. Accordingly, the iodinated polymer of the invention is substantially non-water swellable.

The general structural formula of iodinated polymers of the invention is represented by structural formula I above. The backbone chain of the iodinated polymer can represent:

(i) a condensation polymer such as a polyester, polyamide, polyurethane, polycarbonate, polyepoxide, polyether, a phenol-formaldehyde polymer, and equivalent condensation polymers;

(ii) an addition polymer produced by the polymerization of one or more addition polymerizable monomers containing a polymerizable unsaturated double bond, e.g., vinyl monomers, including such addition polymers as poly(vinyl alcohol), poly(alkylmethacrylates), poly(alkylacrylates), and equivalent addition polymers; or (iii) a naturally occurring polymer, for example, a polysaccharide containing repeating glucose units such as starch, glycogen, cellulose, cellulosic derivatives, and equivalent naturally occurring polymers.

Preferably, repeating unit A of formula I represents the residue of a repeating unit having an appended hydroxyl group, such as the repeating unit of poly(vinyl alcohol), the repeating epoxy unit of a polyepoxide, the repeating unit of a hydroxylated acrylic polymer such as poly(hydroxyethylacrylate), or the repeating glucose unit of a naturally occurring polysaccharide. The appended hydroxyl group can serve either as a crosslinking site or as a reaction site for precursor compounds of the organic moiety X in formula 1. Such precursor compounds can be chemically linked to the repeating units of the polymer backbone chain through a condensation reaction with the appended hydroxy group.

The organic moiety X of formula I above represents an iodine-containing organic fragment comprising an iodinated aromatic group and one or more hydrophilic groups. To obtain the high iodine content characteristic of the polymers used in the invention, the iodinated aromatic groups have multiple iodine substituents bonded directly to the aromatic carbon ring atoms. Especially preferred among these iodinated aromatic groups are aromatic groups containing three, preferably four, carbon ring atoms substituted by iodine. A preferred iodinated aromatic group is an iodinated phenyl ring, although naphthyl rings and nitrogen-containing heterocyclic rings containing 5 to 7 ring atoms can also be used. An especially preferred iodinated aromatic group is a phenyl ring bearing iodine substituents on 4 of the carbon ring atoms.

The hydrophilic group(s) of X are typically present as a substituent(s) bonded directly, or indirectly through a chemical linking group, to one or more of the carbon ring atoms of the iodinated aromatic group. Preferred linking groups include short chain aliphatic groups, e.g., alkylene groups, amido groups and equivalent aliphatic groups, having 1 to 4 carbon atoms. Typical hydrophilic groups can be selected from a variety of such groups including carboxyl groups; sulfo groups; amino groups; salts thereof such as carboxylate salts, sulfonate salts, ammonium salts; polyols such as glucose groups; and equivalent hydrophilic groups.

Typically, the precursors from which the organic moiety X of formula 1 is derived contains a reactive group which forms a chemical linking group with the repeating unit of the polymer backbone chain. In the preferred embodiment of the invention wherein the repeating unit of the polymer backbone chain represents the residue of a repeating unit bearing a hydroxyl group, the reactive group contained on the precursor of X is a group reactive with this hydroxy group. For example, the reactive group can be a carboxyl group which condenses with the appended hydroxy group of the backbone chain to form an ester group linking an iodinated aromatic moiety to the polymer backbone. A variety of other reactive groups which react with a hydroxy group to form such chemical linking groups as ethers, amides, thioesters, carbonates, carbamates, sulfides, and equivalents, can also be used.

A partial listing of precursors for the moiety X of formula I includes, for example, 3-(3-amino-2,4,6-triiodophenyl)-2-ethylpropionic acid; 3-(3-hydroxy-2,4,6-triiodophenyl)-2-ethylpropionic acid; sodium 3-(3-butyrylamino-2,4,6-triiodophenyl)-2-ethylacrylate; 3,5-diiodo-4-pyridone-N-acetic acid; 3-acetamido-2,4,6-triiodobenzoic acid; tetraiodophthalic anhydride; and the like. Tetraiodophthalic anhydride can be particularly useful because of its high iodine content.

Based on the foregoing description, a structural formula of certain preferred iodinated polymers can be illustrated as

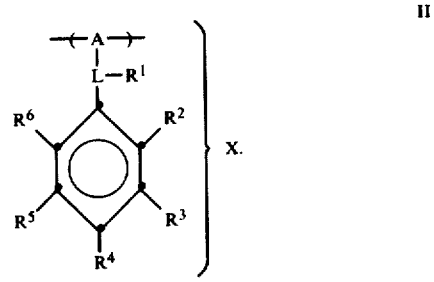

wherein:
A is as defined in formula I above;
X is as defined in formula I above;
L represents one of the above-described linking groups, e.g., ester, ether, amide, thioester, carbonate, carbamate, sulfide, and the like; and each of $R^1$ to $R^6$, which may be the same or different, represents hydrogen, an iodine-containing substituent, or a hydrophilic group-containing substituent, with the proviso that the iodine content of X is from about 40 to 80 percent (based on the molecular weight of X).

Preferred iodinated polymers are crosslinked. This can enhance the water-insolubility and resistance to swell properties of the polymer. Crosslinking can be effected by incorporation of suitable crosslinking sites either on the polymer backbone chain or on the moiety X or both. For example, in a preferred embodiment wherein the polymer contains a repeating backbone unit bearing an appended hydroxyl group and a sidechain group X containing a carboxyl group as a hydrophilic group, a hydroxyl group appended to the backbone chain of one polymer can react with the carboxyl group attached to the sidechain X of another polymer, thereby crosslinking the two polymers through an ester linkage.

The polymeric contrast agents of the invention contain both hydrophilic and hydrophobic groups. Repeating backbone units A of formula I are substantially hydrophobic as are many portions of the moiety X. Of course X also contains one or more hydrophilic groups. This combination of hydrophobic and hydrophilic groups is believed important to provide the proper polymer surface and electrical characteristics which, in turn, provide proper polymer compatibility with body organs and tissues.

The iodinated polymers can be prepared by any of a variety of conventional polymerization and chemical reaction techniques. A preferred reaction sequence is to chemically react precursor compounds for the sidechain group X with a preformed polymer containing appended groups serving as suitable reaction sites, e.g., hydroxyl groups. The preformed polymer can be prepared by addition or condensation polymerization, depending on the polymer; or it can be obtained from naturally occurring sources in the case of naturally occurring polymers, e.g., polysaccharides. The precursor compounds for the moiety X can be reacted with the reaction site on the polymer backbone by a variety of well-known reaction procedures, depending on the nature of the linking group L in formula II above which is formed in this reaction. Advantageously, the reaction of these precursor compounds is carried out under emulsifying conditions so that the resultant polymers are obtained in finely-divided particulate form. Crosslinking can be carried out during or following attachment of the moiety X to the polymer backbone.

Having obtained a water-insoluble and non-water-swellable iodinated polymer as described above, the polymer can be subjected to grinding or milling treatment to obtain polymer particles of the appropriate size range. Of course, in cases where the polymers are prepared under suitable conditions, such as bead polymerization or emulsifying conditions, the polymer may already have an appropriate particle size so that additional milling or grinding may be unnecessary. A useful particle size for these polymer particles is within the range of from about 0.01 to 1000 microns, preferably 0.1 to 100 microns. Small particle sizes within the range of from 0.1 to 5 microns are especially preferred where the polymer particles are to be used as contrast agents for injection into blood vessels and other small orifice body organs.

A preferred embodiment of the invention provides a radiographic contrast composition comprising finely-divided particles of the above-described iodinated polymer, as contrast agent, dispersed in an aqueous liquid which serves as the carrier for the contrast agent. These dispersions typically have a relatively low viscosity at room temperature (22° C.) on the order of about 0.3 cp to 1000 cp. This makes these dispersions useful as contrast agents which may be injected into the bloodstream and used for X-ray visualization of certain blood vessels or for X-ray visualization of certain body organs which concentrate contrast agents injected into the bloodstream, e.g., the liver.

Typical radiographic contrast compositions comprising aqueous dispersions of the iodinated polymer described herein contain a radiographically effective amount of the polymer within the range of from about 10 to 50 weight percent based on the total weight of the dispersion.

The carrier employed in the radiographic contrast compositions of the invention can be either liquid or dry. Typically, the carrier is liquid at the time the contrast agent is injected into the body of the test subject. In such case, the carrier is typically an aqueous liquid, including an optional buffer and any other additives as described hereinafter. Alternatively, the radiographic contrast composition of the invention can be prepared in dry form, for example, as a dry powder or in dry tablet form. In dry form a carrier for the polymer contrast agent can also be used, for example, a suitable binder such as a natural or synthetic polymer.

In still other embodiments, an element comprising the iodinated polymer contrast agent described herein and a suitable dry carrier are provided. For example, the element can be a surgical element which contains the iodinated polymer described herein as a contrast agent and a carrier such as a surgical instrument, dressing, suture, implant, and the like. In such case, the presence of contrast agent in or on the carrier enables one to readily identify and locate the position of the element within a body portion of a patient.

The iodinated polymers can, of course, be admixed with one or more of the various conventional additives used to control and enhance the properties of radiographic contrast agents. For example, thickening agents are typically incorporated where it is desired to use the contrast agent in a gastrointestinal radiographic contrast composition. Buffers, viscosity regulating agents, suspending agents, peptizing agents, anti-clotting agents and other drugs, mixing agents, and the like can also be added. A partial listing of certain specific additives includes gums, sugars, gelatin, sodium alginate, agar, albumin, dextrin, pectin, and sodium carboxymethyl cellulose. It will be understood that such additives as well as various grinding agents, surface active agents, sweetening agents, flavoring agents, preservatives and the like can be incorporated in the radiographic contrast compositions of the invention. Such additives are conventional in the art and further detail concerning the use and type of these additives may be found by reference to Miller and Skucas, *Radiographic Contrast Agents,* supra.

The method of forming a radiographic image by use of the contrast agents of the invention can be carried out in accord with established radiographic techniques and procedures. Thus, the method includes the steps of introducing the contrast agent into a body portion of the test subject, exposing that portion of the test subject containing the introduced contrast agent to X-rays to produce an X-ray image pattern corresponding to the presence of the contrast agent, and visualizing this image pattern, the specific improvement afforded by the image-forming method of the invention being the introduction of the above-described iodinated polymer as all or part of the contrast agent.

The introduction of the iodinated polymer contrast agent into the body of the test subject can be accomplished orally, by use of an enema, by a syringe or by other known techniques. Typically, the contrast agents are introduced in the form of an aqueous suspension; however they could also be administered in dry tablet form or in admixture with a suitable foodstuff. The dosage level, as will be readily appreciated, is in large part determined by the size and surface area of the body cavity or organ to be visualized, the size and weight of the test subject, and the size and type of radiograph desired. For example, when the radiographic contrast compositions are employed as gastrointestinal contrast agents, a typical adult dosage would be in the range of from about 10 to about 100 g. of contrast agent.

Visualization of the X-ray image can be carried out by well-known techniques including the use of a conventional X-ray sensitive phosphor screen—silver halide photographic film combination; various electrophotographic techniques such as xeroradiography; and other radiographic visualization techniques such as computerized axial tomography and ionographic techniques.

The following example is presented to further illustrate one specific embodiment of the invention:

EXAMPLE

Five and one-half grams of poly(vinyl alcohol), PVA, purchased under the trademark Elvanol 52-22 from DuPont was swelled with stirring overnight in 300 ml of pyridine. The mixture was stirred for 4 days at room temperature with 65 g of tetraiodophthalic anhydride to react the PVA with the anhydride. The mixture was then heated to 60° C. for 8 hours to effect crosslinking. A copious precipitate of the iodinated polymeric reaction product formed. This was filtered off and washed with water and dried. Analysis showed that the polymeric reaction product had an iodine content of 61.7 percent compared with a theoretical value of 73.0 percent for complete reaction. The structure of a repeating unit of this iodinated polymeric reaction product was as follows:

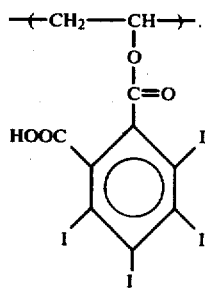
III

The iodinated polymer reaction product having a particle size range of about 1 to 100 microns was stirred in a Waring Blendor with an equal weight of 0.05 M pH 7 phosphate buffer containing 0.15 M sodium chloride and 0.5 percent (by weight of water) of guar gum (Stein and Hall Jaguar A-20-A) thickening agent to form an aqueous suspension radiographic contrast composition. Approximately 30 g. of the mixture was then fed to a starved rabbit. After feeding, a radiograph was taken which showed good visualization of the stomach area of the rabbit.

The radiograph was made using a phosphor screen-silver halide photographic film combination as follows: A DuPont PAR Speed ® Screen (calcium tungstate) was used with Kodak 4517 X-OMAT RP film. The film was exposed with 70 kVp X-rays at 100 mA filtered by ½ mm. copper and 1 mm. aluminum. The distance from the X-ray source to the screen was 150 cm. The exposure time was 0.3 seconds. The film was processed for 90 seconds in a Kodak M6 X-OMAT Processor with Kodak MX-810 Developer in the usual cycle.

The invention has been described in detail with particular reference to certain preferred embodiments thereof, but it will be understood that variations and modifications can be effected within the spirit and scope of the invention.

I claim:

1. A radiographic contrast composition comprising a radiographically effective amount of a contrast agent and a carrier for said agent, said contrast agent comprising a water-insoluble, non-water-swellable iodinated polymer having an iodine content in excess of 35 wt%, said polymer being cross-linked and containing a repeating unit of the formula

wherein
A represents the residue of a repeating unit in the backbone chain of said polymer and bears appended hydroxyl groups; and
X represents an organic moiety containing an iodinated aromatic group, said moiety being of the formula

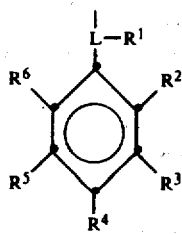

wherein
L represents a linking group selected from the class consisting of ester groups, ether groups, amide groups, thioester groups, carbonate groups, carbamate groups, and sulfide groups; and
each of $R^1$ to $R^6$, which may be the same or different, represents hydrogen, an iodine-containing substituent, or a hydrophilic group-containing substituent, with the provisos that (i) the iodine content of X is within the range of from 40 to 80 wt%; and (ii) said hydrophilic group is a member selected from the class consisting of carboxyl groups, sulfo groups, amino groups, salts of the aforementioned carboxyl, sulfo and amino groups, and polyol groups.

2. A radiographic contrast composition as defined in claim 1 wherein X represents an organic moiety containing an iodinated phenyl group having (a) at least 3 carbon ring atoms bonded directly to an iodine substituent and (b) a hydrophilic group as a substituent bonded directly or indirectly through a linking group to another carbon ring atom of said phenyl group, said hydrophilic group (b) being a member selected from said class defined in (ii) of claim 1.

3. A radiographic contrast composition as defined in claim 1 wherein said contrast agent is in the form of finely-divided particles dispersed in an aqueous liquid carrier.

4. A radiographic contrast composition as defined in claim 1 wherein said carrier is a natural or synthetic polymer binder and said composition is in dry tablet form.

5. A surgical element comprising a radiographically effective amount of a contrast agent and a surgical article as a carrier for said agent, said contrast agent comprising a water-insoluble, non-waterswellable iodinated polymer having an iodine content in excess of 35 wt%, said polymer being cross-linked and containing a repeating unit of the formula

wherein

A represents the residue of a repeating unit in the backbone chain of said polymer and bears appended hydroxyl groups; and X represents an organic moiety containing an iodinated aromatic group, said moiety being of the formula

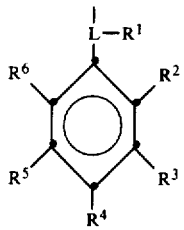

wherein

L represents a linking group selected from the class consisting of ester groups, ether groups, amide groups, thioester groups, carbonate groups, carbamate groups, and sulfide groups; and each of $R^1$ to $R^6$, which may be the same or different, represents hydrogen, an iodine-containing substituent, or a hydrophilic group-containing substituent, with the provisos that (i) the iodine content of X is within the range of from 40 to 80 wt%; and (ii) said hydrophilic group is a member selected from the class consisting of carboxyl groups, sulfo groups, amino groups, salts of the aforementioned carboxyl, sulfo and amino groups, and polyol groups.

6. A surgical element as defined in claim 5 wherein said carrier is a surgical instrument, dressing, suture, or implant.

7. A method of forming a radiographic image of a body portion of a test subject which comprises (a) introducing a radiographically effective amount of a contrast agent into said body portion, said contrast agent comprising a water-insoluble, non-water-swellable iodinated polymer having an iodine content in excess of 35 wt%, said polymer being cross-linked and containing a repeating unit of the formula

wherein

A represents the residue of a repeating unit in the backbone chain of said polymer and bears appended hydroxyl groups; and X represents an organic moiety containing an iodinated aromatic group, said moiety being of the formula

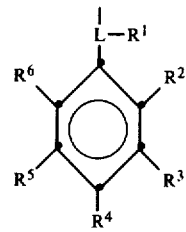

wherein

L represents a linking group selected from the class consisting of ester groups, ether groups, amide groups, thioester groups, carbonate groups, carbamate groups, and sulfide groups; and each of $R^1$ to $R^6$, which may be the same or different, represents hydrogen, an iodine-containing substituent, or a hydrophilic group-containing substituent, with the provisos that (i) the iodine content of X is within the range of from 40 to 80 wt%; and (ii) said hydrophilic group is a member selected from the class consisting of carboxyl groups, sulfo groups, amino groups, salts of the aforementioned carboxyl, sulfo and amino groups, and polyol groups;

(b) exposing said body portion containing said contrast agent to X-rays to form an X-ray image pattern corresponding to the presence of said contrast agent, and (c) visualizing said image pattern.

* * * * *